United States Patent [19]

Metzner et al.

[11] Patent Number: 4,797,191

[45] Date of Patent: Jan. 10, 1989

[54] MEASURING DEVICE FOR DETERMINATION OF THE ACTIVITY OR OF THE CONCENTRATION OF IONS IN SOLUTIONS

[75] Inventors: Klaus Metzner, Bad Homburg; Detlef Westphal, Oberursel; Wolfgang Allendörfer, Bad Homburg; Reinhard Hahnel, Lollar; Hans-Dietrich Polaschegg, Oberursel, all of Fed. Rep. of Germany

[73] Assignee: Fresenius AG, Fed. Rep. of Germany

[21] Appl. No.: 732,022

[22] Filed: May 8, 1985

[30] Foreign Application Priority Data

May 8, 1984 [DE] Fed. Rep. of Germany ....... 3416956

[51] Int. Cl.⁴ .......................................... G01N 27/26
[52] U.S. Cl. .................................. 204/411; 204/409; 204/1 T
[58] Field of Search ................... 204/1 T, 409, 411

[56] References Cited

U.S. PATENT DOCUMENTS

| | | | |
|---|---|---|---|
| 3,151,052 | 9/1964 | Arthur et al. | 204/409 |
| 3,556,950 | 1/1971 | Dahms | 204/1 T |
| 4,202,747 | 5/1980 | Buzza et al. | 204/411 |
| 4,206,027 | 6/1980 | Schindler et al. | 204/411 |
| 4,218,197 | 8/1980 | Meyer et al. | 204/411 |
| 4,236,988 | 12/1980 | Suzuki et al. | 204/1 T |
| 4,253,847 | 3/1981 | Matson et al. | 204/1 T |
| 4,283,262 | 8/1981 | Cormier et al. | 204/411 |
| 4,424,276 | 1/1984 | Clark et al. | 204/1 T |
| 4,627,893 | 12/1986 | Cormier et al. | 204/411 |

FOREIGN PATENT DOCUMENTS

| | | |
|---|---|---|
| 377366 | 3/1985 | Austria . |
| 2726772 | 1/1979 | Fed. Rep. of Germany . |
| 2908719 | 9/1979 | Fed. Rep. of Germany . |
| 3206049 | 9/1983 | Fed. Rep. of Germany . |
| 132210 | 9/1978 | German Democratic Rep. . |

Primary Examiner—John F. Niebling
Assistant Examiner—Steven P. Marquis
Attorney, Agent, or Firm—Andrus, Sceales, Starke & Sawall

[57] ABSTRACT

Measuring device for determination of the activity or of the concentration of ions in solutions, which has an electrode block having several electrodes and with a flow channel, the flow channel being in connection at its one end with a sample vessel and is connected at its other end to a line, in which a pump is interposed, with calibrating solution containers.

Between the pump and the outlet of the electrode block branches off a discharge line, in which a further pump is interposed. Preferably, both pumps are combined into a peristaltic pump, the lines being laid in the segments of the pump.

According to a second embodiment, the electrode block is again in connection with the calibrating solution containers. The delivery of the sample is performed however on the same side through a septum. Advantageously, the other side of the electrode block opens out into a pressure equalization vessel, into which a withdrawal line opens in which in turn the above mentioned peristaltic pump is interposed.

15 Claims, 5 Drawing Sheets

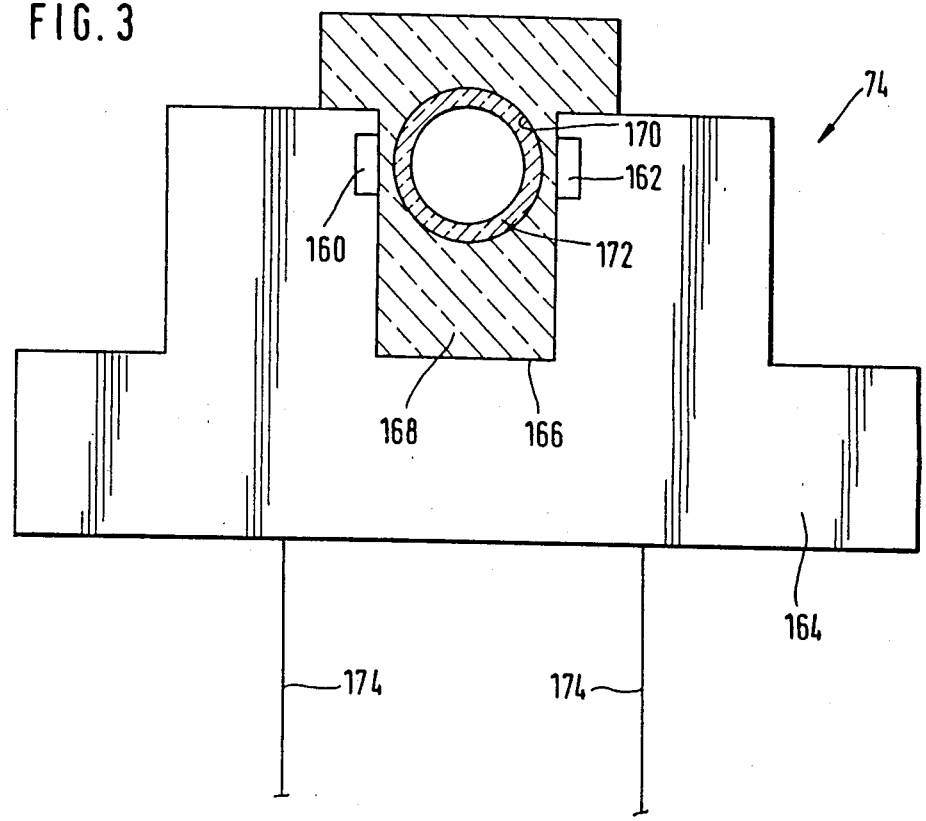
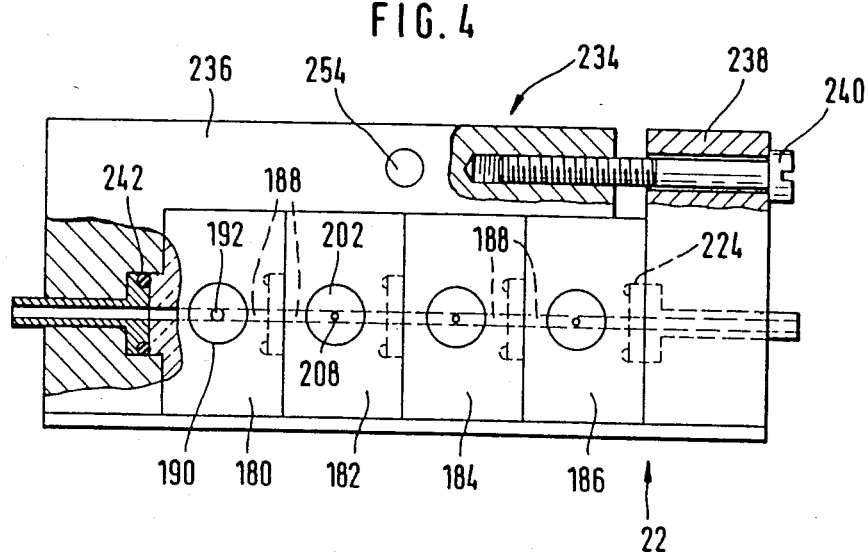

MEASURING DEVICE FOR DETERMINATION OF THE ACTIVITY OR OF THE CONCENTRATION OF IONS IN SOLUTIONS

The invention relates to a measuring device for determination of the activity or of the concentration of ions in solutions, with at least one measuring electrode and a reference electrode, which are connected to each other by a flow channel, the first outlet of which is in connection with the environment and the second outlet of which is connected by a first line, in which a first pump and at least one valve are interposed, to at least one calibrating solution container.

A measuring device of the type mentioned at the start is known for example from U.S. Pat. Nos. 4,206,027, 3,151,052 and 3,556,950 as well as from the monograph by Karl Cammann. "Das Arbeiten mit ionenselektiven Elektroden" (Working with ion-selective electrodes), Springer-Verlag 1977. pp. 190–194.

Each of these devices consists of a plurality of electrodes which are arranged adjacently and are in connection with one another by a flow channel. They thus form a flow arrangement which is in connection on the one side via a line to containers which have one or more standard solutions and a measuring solution and on the other side to a pump. To bring the containers into connection with the flow arrangement, a multi-way valve is provided in the connecting line to the flow arrangement and is opened or closed appropriately by a control unit.

Such a flow arrangement can have several different electrodes, for example ion-selective electrodes, which for the measurement of a special ion type, for example of the sodium or potassium order, regularly have a reference electrode as a reference point.

With such an arrangement, first the measurement of the sample is performed, followed by the calibration. This involves initially switching in a first standard solution via the multi-way valve to the feed line and then pumping it by the pump into the flow arrangement and there after performing calibration of the entire system.

The same way is used to perform the calibration of a second or further standard solution, which remains in the arrangement until the next measurement.

Such a calibration and measurment is, in the case of the known device, on the one hand very elaborate and on the other hand beset by considerable errors. This is attributable, for example, to the fact that remains of the last-determined liquid stay in the feed tube to the flow system and in the flow system itself, with the consequence that the following liquid is contaminated by the previously measured liquid. Consequently, the entire feed line and the flow system itself must initially be rinsed with the other solution for a long enough time to ensure the complete removal of remains of the previously measured solution.

Such a procedure is both time-consuming and uses a great deal of materials so that, regarded all in all, the operation of such a device is disadvantageous.

In the case of a further known device, the pump is provided upstream of the flow device in the feed line, while the sample connection is located downstream of the flow arrangement.

In this device, the calibrating solutions are displaced into the flow arrangement by clockwise rotation of the pump, while the sample is drawn into the flow arrangement by counter-clockwise rotation of the pump and displaced out of the flow arrangement through the pump into the waste. Just as in the case of the device explained above, a multiway valve or a branch of several lines, in each of which a valve is interposed, is provided upstream of the pump.

This arrangement also has the disadvantage that, after suction removal of the sample in the connecting line between the flow arrangement and the multi-way valve, remains of the sample stay behind, which results in an intermixing of the calibrating liquid with the sample remains in the tube and in the multi-way valve during feeding of the first calibrating solution.

Furthermore, there is the possibility that the multiple valve or the manifold is permanently soiled by remains of the sample liquid, for example blood, as the blood becomes ingrained.

The invention is therefore based on the object of developing the measuring device of the type mentioned at the start so that smallest possible quantities of standard and measuring solutions are necessary at as short as possible a time for an exact measurement.

The object is achieved by the characterizing features of claim 1 or 2.

The measuring device according to the invention has, first of all, the advantage that the intermixing regions, i.e. the regions in which an intermixing of the calibrating solutions and the measuring solution inevitably occurs, are kept as small as possible. This is achieved in a first embodiment by the feed line for the calibrating solutions having next to the inlet of the measuring device a branching-off line which serves to carry away the measured liquid (calibrating solution or measuring solution). Consequently, the entire feed line no longer comes into contact with the solution to be measured.

The region through which all liquids have to flow thus remains substantially confined to the flow channel of the measuring arrangement.

Furthermore, in the branch-off line is provided a pump with which the liquid to be pumped away is displaced through the measuring device and the branch-off line. This pump is to have at least the same displacement capacity as the pump arranged in the feed line.

Advantageously, a single pump in the form of a peristaltic roller pump is used which acts on both sides, ie. both the feed line and the removal line are each laid in a pump segment of the roller tube pump. By appropriate selection of the internal diameter of the tubes, the same or varying displacement volumes can be determined. Preferably, the feed tube has a smaller internal diameter than the removal tube. i.e. the displacement volume of the removal tube is greater than that of the feed tube. Furthermore, in the first embodiment it is possible to prevent a contaminated calibrating solution flowing into the flow arrangement. This can be achieved by the pump acting on both sides pumping the calibrating solution up to the branch point. Due to the pump action of the other pump segment, the fed calibrating solution is pumped away through the branch-off line, so that this causes the calibrating solution to be pumped past the flow arrangement into the discharge. This pump action is continued until and sizeable contaminants in the feed branch are removed. Subsequently, a valve arranged in the discharge branch downstream of the pump segment is closed, with the consequence that this pump segment no longer continues to displace. This results inevitably, in the pumping in of the pure calibrating solution into the flow arrangement as the one pump segment in the feed line continues to displace.

The displacement of the calibrating solution carries on until the flow channel in the measuring device is completely filled. Subsequently, the valve arranged on the outlet side of the container with the calibrating solution is closed.

It is advantageous if the roller tube pump remains in operation after closing this valve and, due to the constant occlusion of the tube, generates a pulsing of the liquid column in the tube and in the flow arrangement. This results, in particular in the flow arrangement, in all remaining coarse contaminants, in other words also those sample ingredients left adhering to the wall of the flow channel, being taken up by the calibrating solution and distributed in it.

If the valve in the discharge line is then opened again an underpressure is generated in the entire flow arrangement, with the consequence that the liquid column in the entire flow channel is displaced into the discharge. This occurs with the valves provided in the feed line closed.

Thereafter, the discharge valve is closed and the valve downstream of the container with the calibrating solution is reopened. causing pure calibrating solution to flow into the flow channel again. In this step, there is therefore, within the measuring limits, pure calibrating solution in the flow arrangement, so that the calibration of this flow arrangement can then be performed.

After the calibration with a first calibrating solution, the above steps are repeated for calibration with a second or further calibrating solution.

After conclusion of calibration, establishment of the measured value is performed. This is followed by a new measuring cycle, consisting of introduction of the measuring solution into the measuring device and calibration. The feed of the measuring solution is performed from the other orifice of the feed channel through a continuing capillary operation of the pump on the side of the discharge line, in which the valve is open. After filling the channel, measurement of the parameters is performed with the aid of the electrodes and the electrically downstream evaluation unit.

After measurement, calibration is then performed again with the calibrating solutions, as has been described above.

In a further expedient embodiment, another line, in which a valve is likewise interposed, is provided on the feed side of the calibrating solutions. Air can be fed through this line and this air feed has the advantage that only a certain liquid quantity can be pumped in each case through the feed line without closure of the valve assigned to the respective calibrating solution container causing a standstill of the displaced liquid column due to underpressure.

Consequently, in this embodiment a considerable quantity of liquid can be saved by venting the system.

In a second preferred embodiment of the measuring device according to the invention, the displacement of the liquids through the flow channel is performed only in one direction. In the case of this embodiment, one end of the flow channel of the measuring device according to the invention is connected to a feed line from which lines branch off in each case which are connected to calibrating solution containers or to the surroundings (air). These branching-off lines can be blocked off by corresponding valves. Downstream of these valves there is interposed again in this line a pump, via which the fluids to be displaced are displaced into the measuring channel.

On the other side of the measuring channel the removing line opens out into a collecting vessel, so that the pressure fluctuations in the channel are reduced. This collecting vessel is connected to a discharge line, in which a pump is interposed. It is advantageous if this pump is combined together with the pump in the feed line into a pump acting on both sides, as explained above in the case of the first embodiment.

The feed of the measuring solution is performed on the side of the feed line directly into the measuring channel by a cannula being pierced through a septum arranged ahead of the measuring channel and introduced into the measuring channel. This arrangement is particularly advantageous in the case of blood withdrawals by means of a syringe, which can then be introduced directly into the measuring channel.

Further features, advantages and embodiments of the invention are explained in the following description with reference to the drawing in which:

FIG. 3 shows a section through the light barrier arrangement according to FIG. 1 along the line III—III.

FIG. 4 shows a plan view of the electrode block according to FIG. 1 or 2.

FIG. 1 shows a measuring unit 20 which represents the first preferred embodiment of the invention.

This measuring unit 20 has an electrode block 22, which is composed in example 2 of four individual electrodes. Such an electrode block is explained below, as shown in FIG. 4.

Passing through this electrode block 22 is a flow channel 24, all electrodes each having a part of this flow channel. When composing the electrodes, these parts are flush with each other in axial alignment and thus form the flow channel 24.

The flow channel 24 has in the electrode block two end regions 26 and 28, which are in each case connected to branching-off lines 30 and 32.

Figure 1:
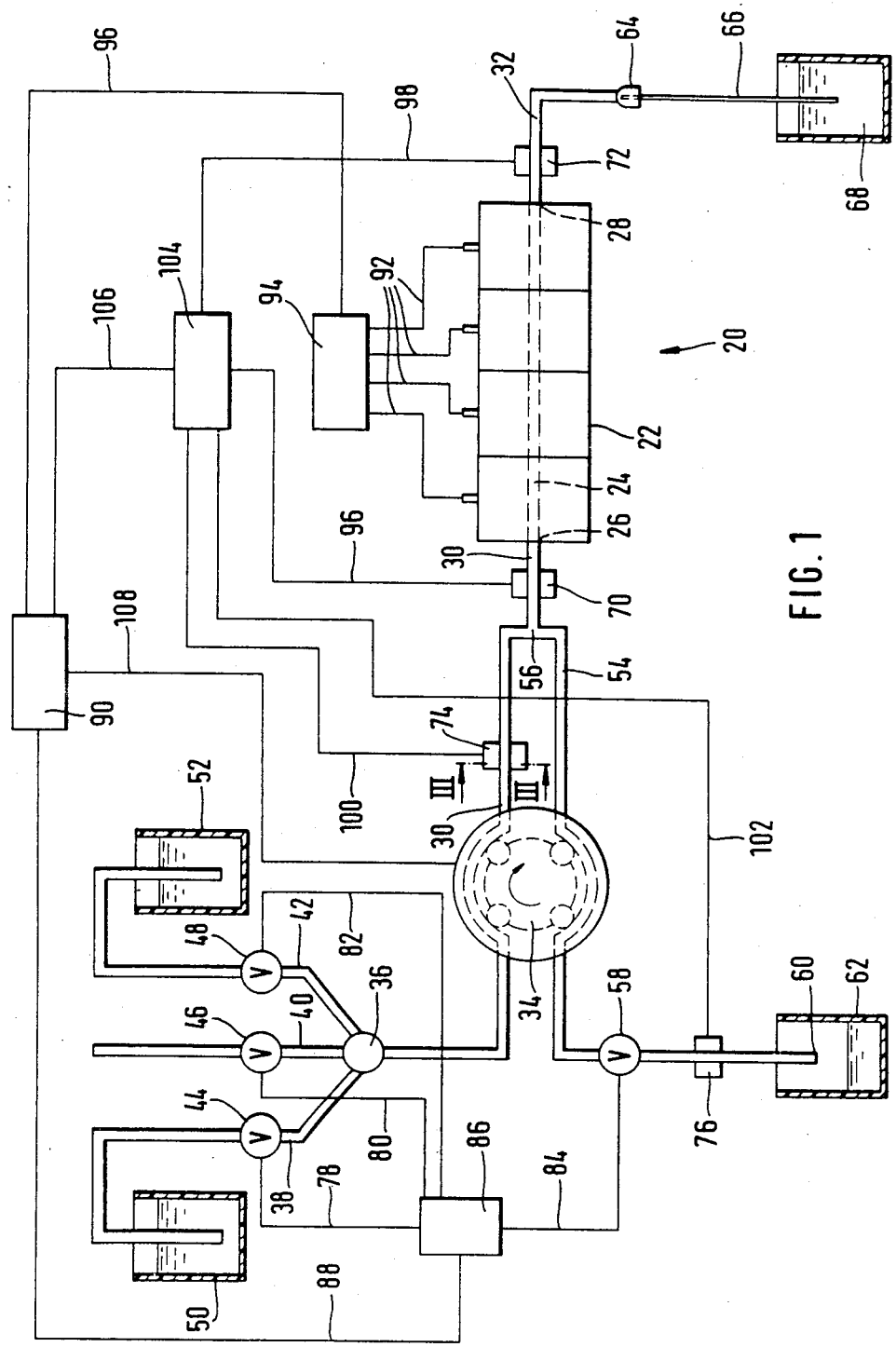
FIG. 1 shows diagrammatically the measuring device according to the invention as in a first embodiment.

The line 30 thus extends away from the end region 26 and passes through a pump 34, which is advantageously designed as a peristaltic roller tube pump, the line being laid in one segment, as shown in FIG. 1. Upstream of the pump, the line 30 has a branc or mixing point 36, from which several lines branch off, namely lines 38, 40 and 42. Interposed in each of these lines 38–42 is a shut-off element 44, 46 and 48.

The end of the line 38 is connected to a vessel 50 for a first calibrating solution, while the line 42 is connected to a vessel 52 with a second calibrating solution. The line 40 represents an air connection, in other words is pressure-equalized in connection with the environment.

Between the pump 34 and the end region 26 of the electrode block 22, a discharge line 54 branches off from the line 30 at the branch point 56. Just as the line 30, this line 54 is laid into the pump 34, so that here too a pump segment of the pump 34 can again act on the line 54. Thus, the pump 34, which is advantageously designed as a peristaltic tube pump, acts on both sides. Of course, this two-sided pump 34 may also be replaced by two pumps, each acting on the lines 30 and 54, respectively.

Since, when using a peristaltic tube pump 34, the displacement capacity of the lines 30 and 54, advantageously in the form of tubes, depends on the internal cross-section of the tube used, it is preferred that the line 54 permits at least the same displacement volume as the line 30. In particular, the displacement volume of the line 54 is greater than that of the line 30, ie. the internal cross-section of the line 54 is greater than that of the line 30. In a similar way, the displacement volume of separate pumps is designed such that the pump in connection with the line 54 has at least the same displacement volume as that of the pump used in the line 30. Preferably, the displacement volume of the two pumps is equal.

Interposed in the line 54 downstream of the pump 34 is a valve 58.

The line end 60 of the line 54 opens out into a waste container 62, which serves to receive the used liquids.

The other end region 28 of the electrode block 22 is—as already mentioned above—connected via a line 32 to an adaptor 64, which is designed in such a way that it can receive an exchangeable aspiration cannula 66.

Both the line 32 and the aspiration cannula 66 are preferably of flexible form so that this entire arrangement can be disposed in any way. It is expedient if the aspiration cannula 66 takes the form of a flexible plastic pipe which can be exchanged again after being used once.

On the other hand however, the cannula of a syringe, which has been used for example for blood withdrawal, may also be inserted into the adaptor 64.

As shown in FIG. 1, the aspiration cannula 66 can dip into a container 64 which contains the liquid to be subjected to measurement.

Alongside the end regions 26 and 28, the lines 30 and 32 each have sensors 70 and 72, with which the positioning of the liquid columns arriving through the lines 30 and 32 can be reliably detected and monitored. It is advantageous if IR light barriers are used as sensors 70 and 72.

Another such sensor 74 is arranged in the line 30 between the pump 34 and the branch point 56. Finally, there is another sensor 76 in the region of the line 54 between the valve 58 and the line end 60.

The last-mentioned sensors are also advantageously designed as IR light barriers.

The sensors 70 and 72 are used to control the correct filling of the measuring capillaries, the aspiration cannula, the line 32, the flow channel 24 and the line 30.

The sensor 74 serves as a monitor for the supply of the calibrating solutions from the containers 50 and 52 or of the air.

The sensor 76 advantageously controls the discharge line 54 and, by reverse-pumping of the pump, in other words by changing the rotational direction of the pump, verifies whether the waste container 62 is filled. For this purpose, the line end 60 of the line 54 is arranged only just below the upper edge of the waste container 62. Whenever waste liquid reaches this line end 60, a signal results at the sensor 76 with drawing up of a corresponding liquid column.

As can be seen from FIG. 1, the valves 44, 46, 48 and 58 are connected via the lines 78–84 to a valve control unit 86, which is connected via a line 88 to a general control device 90.

The electrodes of the electrode block 22 are connected via lines 92 to an electrode connection unit 94, which is likewise connected to the control device 90 via a line 96.

Finally, the sensors 70, 72, 74 and 76 are connected via lines 98–102 to a sensor control unit 104, which is connected via the line 106 to the control device 90.

Furthermore, the control device 90 is connected via the line 108 to the motor of pump 34.

Of course, the units 86, 90, 94 and 104 may also be integrated into a single unit, which is preferably the case.

The valves 44–48 and 58 are opened or closed via the valve control unit 86, on command of the control device 90. This control device likewise receives the signal from the sensor indicating unit 104 and evaluates it in an appropriate way, the valve control unit 86 or the motor pump 34 being appropriately driven via the line 108.

Finally, the control unit 90 also receives the signals from the electrode connection unit 94, which converts and evaluates the electrode signals.

The measuring unit 20 shown in FIG. 1 works in the following way:

The use of ion-selective flow electrodes in the electrode block 22 for determination of the activity or of the concentration of certain ion types in solutions requires that, after each sample measurement, a calibration of the electrodes is carried out with solutions of exactly known composition. For this, after suction removal of the sample, the calibrating liquids must in each case be pumped into the electrode channel, avoiding any eventuality of an intermixing of sample remains and calibrating liquids.

This requirement is met by the measuring unit 20.

For a sample aspiration via aspiration cannula 66, the pump 34 is used to suck the sample out of the container 68, with opened valve 58, as far as the branch 56, the sensors 70 and 72 monitoring the correct filling of the flow channel 24. When the liquid column reaches the sensor 70, the pump continues to be actuated for a certain time interval in order to ensure that remains of the calibrating solutions in the flow channel 24 are completely removed from the measuring region into the discharge line. It is advantageous if, after delivery, the sample is transported on by the length of the aspiration cannula 66. This frees the aspiration cannula 66 and prevents dripping of the sample. At the same time, the first portion of the sample, particularly contaminated by the remaining liquid in the measuring capillary or in the flow channel 24, is pushed out of the electrode block 22 and the sample carry-over is reduced without increasing the sample quantity.

This is followed by measuring the required parameters, the pump 34 beng shut down for this purpose by the control device 90.

After completion of measuring the required parameters, which are advantageously indicated on the electrode connection unit 94, the pump 34 is started up and, with opened valve 58, is operated until the sample has been completely pumped through the discharge line 54 into the waste container 62.

Subsequently, a two-point calibration is advantageously performed after each measurement, so that the current gradient of the electrodes can be taken into account for each ambient condition.

On the other hand however, a one-point calibration may also be carried out, provided that the errors thereby occurring can be estimated.

Two-point calibration dispenses however with the re-calibration necessary in the former process after a certain time or number of measurements and the possibility of increasing errors upon failure to perform this measure. It merely assumes the same temperature of sample and calibrating liquids, which usually can be guaranteed as the measuring unit 20 is usually at ambient temperature and has a considerably greater thermal capacity than the sample (typically a few 100 μl). For example, a blood sample of 37° C. assumes ambient temperature within seconds.

The conductivity and the ionic activity coefficients likewise have a clear temperature dependence. Usually, these parameters are measured at an ambient temperature to be determined and are converted numerically or electrically to the value of 25° C.

In the case of the two-point calibration used advantageously here, such a temperature compensation is substantially unnecessary. If sample and calibrating liquids have sufficiently accurately coinciding temperatures and temperature coefficients, the exact determination of activity and conductivity of the calibrating liquids at a certain temperature, for example at 25° C., suffices.

In this operation, the voltages of the electrodes in the applied sample at any temperature are compared with those of the calibrating liquids. The 25° C. sample conductance is obtained by linear interpolation between the standard values of the calibrating solutions:

$$LF\,(\text{Sample}) = LF\,(1) + [LF\,(2) - LF\,(1)] \times [U(P) - U(1)]/[U(2) - U(1)]$$

The same applies analogously to the activity A, where it must be taken into account that $$dU = S\,(T) \times \lg\,dA + dU\,(\text{disturbance}).$$

(S: gradient, T: temperature, LF (1) and (2): conductivity value for solutions 1 and 2, respectively; U: potential, P: sample)

Incidentally, this relative method likewise does not take into account the geometry of the LF measuring cell.

After suction removal of the sample, the valve 44 is opened, so that the first calibrating liquid is pumped on through the line 38 into the line 30 as far as the branch point 56 and from there through the underpressure generated in the other pump segment into the line 54. This therefore performs cleaning of the line 30 of remains of the calibrating liquid previously left over.

After a certain time interval, the valve 58 in the discharge line 54 is closed, which causes the calibrating solution to enter into the flow channel 24. The action of the pump is not interrupted until the liquid column of the first calibrating liquid has been pumped through the entire flow channel 24 and has reached the sensor 72, which emits a corresponding signal for closing the valve 44 to the control unit 90. However, the pump 34 continues to pump and, due to its peristaltic character, induces a pulsing in the tube line, so that the entire liquid column intensively wets even the surfaces on which there are usually sample remains. Furthermore, the electrodes therefore already begin at this moment to adjust to the new solution.

After a certain time, the valve 58 in the discharge line is opened again, so that the liquid quantity in the flow channel 24 is suction-removed again.

This is followed by closing of the valve 58 and renewed opening of the valve 44 to feed fresh calibrating solution into the flow channel 24 again. After the stop signal by the sensor 72, actual measuring is then performed by the electrodes of the electrode block 22.

The process described for the first calibrating liquid is applied identically in the case of the second calibrating liquid as well.

The following applies regarding the measuring error due to sample carry-over:

If v is the volume proportion of the remaining sample in the flow channel (via few percent), then the contribution of sample carry-over after intermediate rinsing is estimated as v×v (less than 1°/oo). Thus, the calibrating solution is unfalsified within the measuring accuracy.

Furthermore, the intermediate rinsing causes the electrodes to come into contact with the solution to be measured even before measuring. This increases the time available to the electrodes for adjusting to the new measuring solution and reduces the requirement for measuring time.

The values established in calibration are compared with the values which have previously been stored in the electrode connection unit 94, and if necessary are referred to these values. This is followed by the actual measuring of the sample, after which there is again a two-point calibration.

For the next measurement of a sample, the flexible plastic cannula held in a silicone tube (line 32) or in the adaptor 64 is exchanged. This eliminates a contribution of this cannula to the sample carry-over which occurs with a fixed cannula.

However, it is preferred not to fill the entire line 30 with calibrating liquid. For this purpose, the valves 44 and 48, respectively, are only opened long enough for the liquid quantity necessary for filling the through channel 24 to be withdrawn from the containers 50 and 52, respectively. Subsequently, the valves 44 and 48 are closed and the valve 46 is opened, so that air can enter, i.e. no underpressure can occur in the line 30, which otherwise would hold back the liquid column in the line 30. This valve 46 is then closed when the liquid column has reached the sensor 72. Otherwise, the other operations are the same as in the procedure described above.

Figure 2:
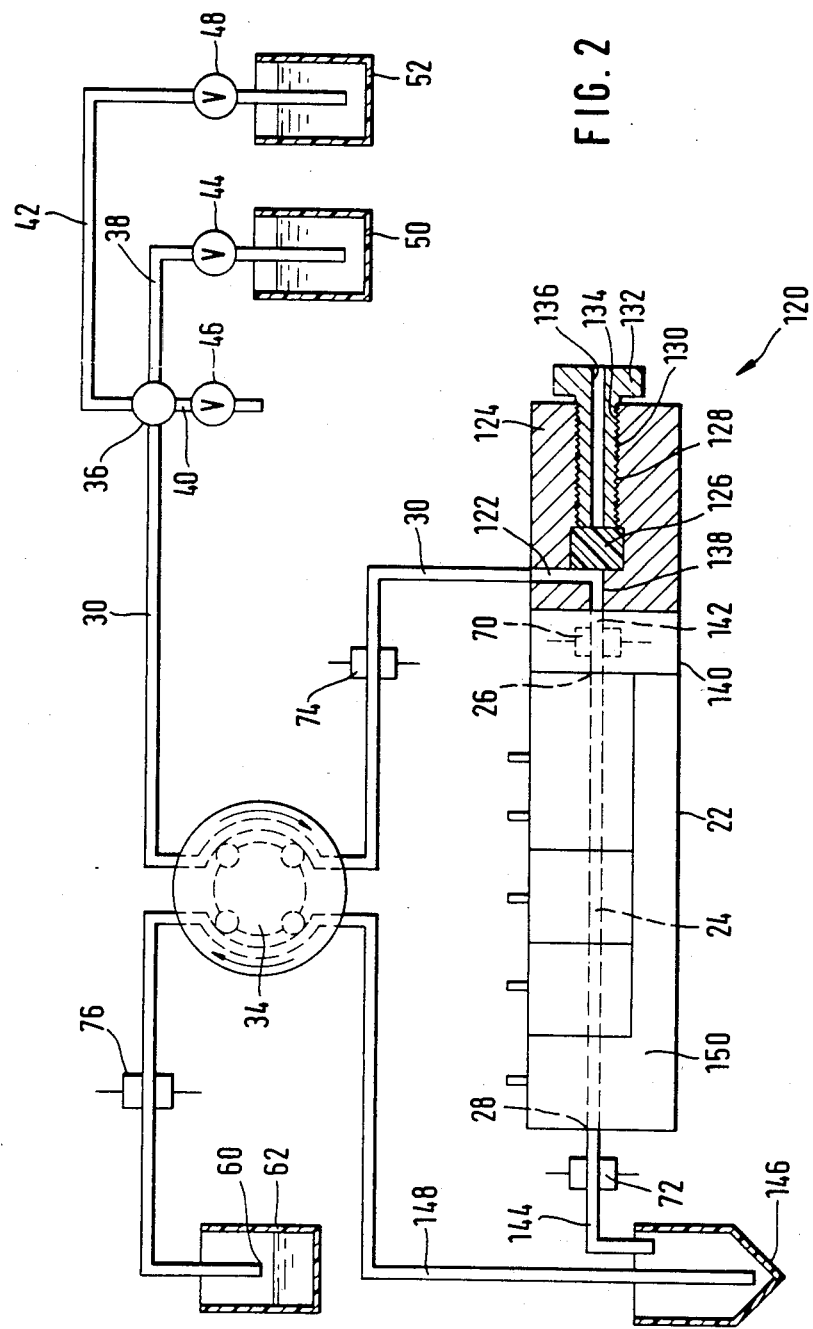
FIG. 2 shows diagrammatically the measuring device according to the invention as in a second embodiment.

FIG. 2 shows a measuring unit 120 which represents the second embodiment of the measuring unit according to the invention. As can be seen in FIG. 2, the same reference symbols as in FIG. 1 have been used for the same parts.

Accordingly, the measuring unit 120 again has an electrode block 22, through which a flow channel 24 passes. The flow channel is again in connection with the feed line 30, in which the sensor 74, a segment of the pump 34, the mixing point 36, the lines 38, 40 and 42, the valves 44, 46 and 48 and the containers 50 and 52 are interposed. However, the line 30 does not open out directly into the end region 26 of the flow channel 24, but-rather is in connection with a channel 122, the axis of which is substantially at right angles to the axis of the flow channel 24 and which is in flow connection with this flow channel 24. This channel 122 is arranged in a septum adaptor 124, which has a septum 126 made of rubber or a plastic and which can be pierced by a cannula tip. The septum is arranged in a corresponding bore 128 in the septum adaptor, the inside surface of which is partially provided with a thread 130. Into this thread can be screwed a stopper 132 which has a corresponding thread 134 and fixes the position of the septum. This stopper 132 has a central channel 136, which is flush with the flow channel 24 and is approximately equivalent in its diameter to the diameter of the flow channel. This channel 136 serves as an introduction aid for an injection needle or the tip of a cannula, which is introduced through the septum into the channel 24. For this purpose, the syringe adaptor is furthermore provided with a channel piece 138, which branches off at right angles from the channel 122 and is flush with the flow channel 24.

There is arranged, furthermore, between the electrode block 22 and the septum adaptor 124 a sensor housing 140, which receives the sensor 70 and likewise has a channel piece 142 passing through it, which in turn is flush with the flow channel 24.

The other outlet or end region 28 is connected to a line 144 which is provided with the sensor 72. This line 144 opens out 1n a pressure equalization vessel 146, which advantageously tapers to a point in the bottom region. The suction removal line 148 is taken to the bottom and is laid in the other segment of the pump 34 and, like the line 54 according to FIG. 1, ends in the waste container 62. Furthermore, in this suction removal line 148 is again arranged a sensor 76, which is arranged in the case of this example downstream of the pump 34, corresponding to the embodiment shown in FIG. 1.

As shown in FIG. 2, the line 144 ends, with pressure equalization, advantageously alongside the end region 28 of the electrode block 22, this end region advantageously being formed at the reference electrode 150 of the electrode block 22. Such an arrangement is therefore of advantage because pressure fluctuations at the reference electrode 150 are to be kept as small as possible. Consequently, the pressure equalization container 146 is located in the direct vicinity of the reference electrode 150 and the end of the tube 144 is at atmospheric pressure. To this extent, only slight pressure fluctuations about this value occur at the membrane of the reference electrode 150, so that an infusion to the reference electrode, and thereby potential jumps and the like, are prevented. Such an infusion would have to have been feared due to the overpressure in the electrolyte line, produced by a pushing of liquid segments through the line. This increases with the length of the line and the number of liquid segments in the line. According to the invention, a drift of the reference electrode attributable to this is prevented by the arrangement of a pressure equalizing vessel 146.

Furthermore, the tube size of the line 148 is dimensioned in such a way that the displacement capacity is greater in the waste line 148 than in the line 144 and the flow channel 24. In this way, overfilling of the pressure equalization container 146 is prevented. It is advantageous if this container consists of a plastic material and is designed to be disposable so that it can be exchanged in the event of faults. Furthermore, neither sedimentation nor nucleation occurs in the pressure equalization container 146 for at least one month if the waste line 148 is taken by a rigid plastic capillary as far as into the tip of the container 146.

As can be seen in the embodiment according to FIG. 2, there is no valve 58, according to FIG. 1, in the waste line 148.

Otherwise, the electrical connection of the individual parts of the measuring unit 120 is identical to the embodiment according to FIG. 1.

As can be seen from FIG. 2, in the case of a sample delivery by means of syringe, the measuring method differs in the following way:

The liquid column is only pushed in one direction through the flow channel 24. At the start, initially the wetting liquid (calibration solution 2) is displaced from the channels 138, 142 and 24 by the air valve 46 being opened. The air is pumped by the pump 34 through the line 30 and the channels 122, 138, 142 and 24 as well as the line 144, and thereby pushes the liquid column ahead of it. This column passes into the pressure equalization container 146 and is pumped into the waste container 62 via the separate pump circuit, which is formed by the line 148. Subsequently, the measuring unit 120 reports readiness for sample delivery. If the product to be measured has been delivered into the flow channel 24 with the aid of a syringe and has reached the sensor 72, the end of the delivery operation is signalled by the measuring unit 120. After a waiting time, in which the electrodes of the electrode block 22 can adjust, the measuring operation begins.

After completion of sample measuring, the pump 34 is again started and the air valve 46 opened, so that the sample is pumped into the pressure equalization container 146 and from there into the waste container 62.

By alternating opening and closing of the air valve 46 and of the valve 44 for addition of the first calibrating solution, liquid segments are pushed through the electrode channel. The large surface tension at the air/liquid transitions takes care that the measuring channel, in other words the flow channel 24, is cleaned well. Furthermore, the separation of the liquid segments by the air in between considerably reduces the liquid exchange between the segments. This process makes possible good cleaning and small sample carry-over with low electrolyte consumption and low metering rate.

After rinsing of the flow channel 24, a sizeable liquid segment is introduced for the measurement from one of the two containers 50, 52 by appropriate opening of the valves 44 and 48, respectively, and is positioned such that the two sensors 70 and 72—as explained below—report solutions, in other words emit a corresponding signal. After the first calibration operation, there then follows calibration with the second calibrating solution, a rinsing operation being performed in each case as an intermediate step. By opening the air valve 46 and pumping with the pump 34, the solution is pumped away out of the flow channel 24. The second calibrating solution itself remains in the measuring unit 120, for wetting the electrodes, until a new measuring solution is fed in. As already mentioned above, for reliable detection and positioning of the liquid columns in the cases of measuring units 20 and 120, sensors 70-76 are used, which are advantageously designed as IR light barriers.

FIG. 3 shows a section through the sensor 74 according to FIG. 1 along the line III—III.

This sensor 74 consists substantially of a photodiode 160, which is arranged opposite a phototransistor 162. Both the photooiode 160 and the phototransistor 162 are arranged in a light barrier housing 164, which has a recess 166, in which a bipartite tube guide 168 is arranged. The side walls of the recess 166 receive the photodiode 160 and the phototransistor 162 in this arrangement.

The tube guide has a bore 170 for receiving the tube 172, which corresponds to the line 30.

The tube guide 168 and the tube 172 are transparent to IR light, so that permanent monitoring is ensured.

The light barrier monitoring means that errors in liquid transport, such as erroneous sample delivery, empty containers for the calibrating solutions, jamming of the valves, air buboles, defective pump tubes etc. can be reliably detected. This, in turn, is prerequisite for a covered installation of the liquid containers, the pump and the tube system, which is indispensable for a transportable bed side unit.

The light barriers have a practically punctiform transmitter and receiver. By suitable introduction of a transparent silicone tube or rf a glass capillary into the beam of rays, as shown in FIG. 3, clearly different output signals are obtained for blood, an aqueous electrolyte solution or air. For instance, a large proportion of the light is absorbed in the case of blood. In the case of an electrolyte solution, on the other hand, the capillary (tube) acts in a similar manner to a cylindrical lens and focuses the light on to the receptor. The latter is designed as a phototransistor and thus only responds weakly in the case of blood, responds strongly in the case of aqueous solutions and has a mid-range response in the case of air. This property can be utilized to distinguish between samples and serves the switching in of special measuring programs for whole blood on the one hand and serum, plasma and electrolyte solution on the other hand.

FIGS. 4–10 show special embodiments of the electrode block and the electrodes contained in this electrode block.

Figure 5:
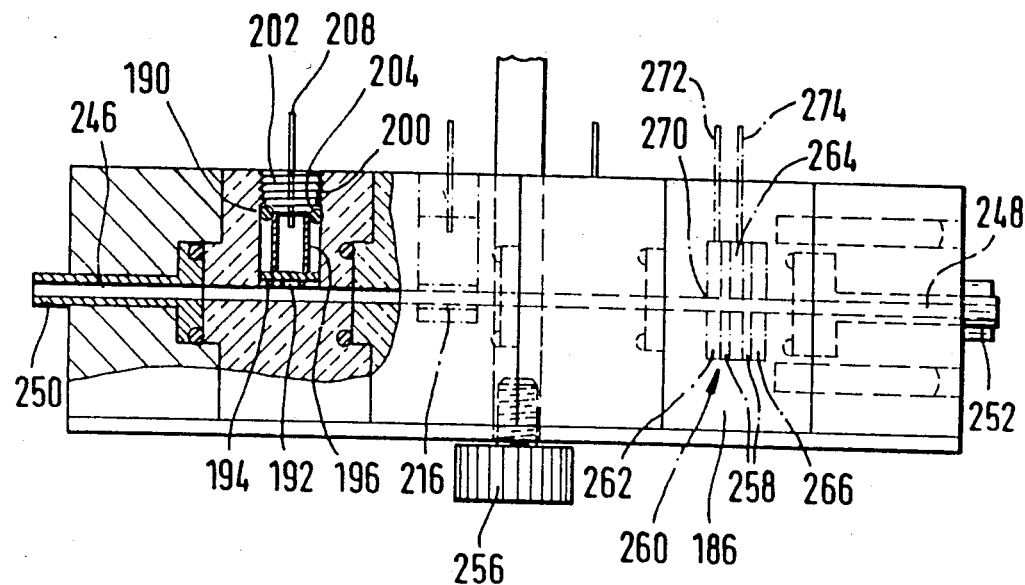
FIG. 5 shows a side view of the electrode block.

FIGS. 4 and 5 show an electrode block 122 in plan view and in side view, respectively, the individual electrodes being shown diagrammatically.

Figure 6:
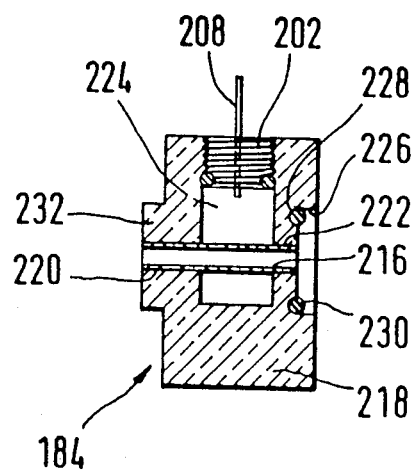
FIG. 6 shows a side view of an individual electrode.

FIG. 6 shows an individual electrode in side view.

As can be seen in FIGS. 4 and 5, the electrode block 122 has four electrodes 180–186, the electrode 180 being explained specifically in more detail and also being illustrated in FIG. 5 as an individual electrode.

Each of this electrodes 180–186 has a cross-bore 188, which forms the through channel 24. In the composed state, the individual cross-bores 188 of the electrodes 180–186 are flush and thus form the through channel 24.

Furthermore, each electrode 180–186 has at right angles to the axis of the cross-bore 188 a bore 190, which leads close up to the cross-bore 188. In order to make a contact with this cross-bore 188, a concentric, but narrower bore 192 is provided in the bore 190.

The bottom region of the bore 190 is substantially covered completely by a liquid-impermeable membrane 194, which advantageously serves as carrier membrane for an ion-selective substance.

Figure 10:
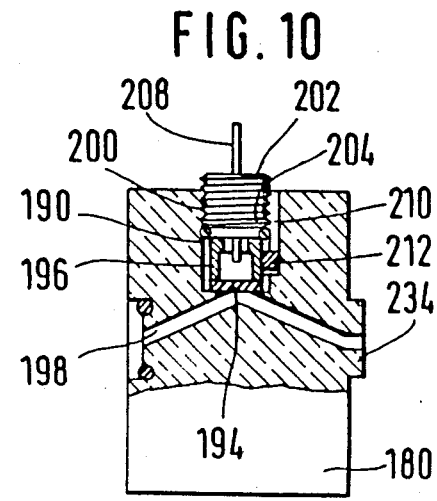
FIG. 10 shows an enlarged cross-section through a part of the reference electrode according to FIG. 8.

Adjoining this membrane 194 is a retaining element 196, in the form of an insert, which is shown in FIG. 5 and FIG. 10. It can also be seen from FIG. 10 that the cross-bore 188 according to FIG. 5 may also be angled in design in the form of an angled cross-bore 198. Such a v-shaped guide has the advantage that the membrane 194 receives a more favourable flow as this design dispenses with the shoulder which is formed by the bore 192 according to FIG. 5.

At its upper edge, the bore 190 has a thread 200, into which a stopper 202 is screwed, which presses the retaining element 196 onto the membrane 194 and fixes the position of the latter.

It is advantageous if the stopper 202 is provided on its side facing the bore 190 with a surrounding annular groove 204, into which an O-ring is inserted, which forms a sealed contact against the wall of the bore 190 when the stopper 202 is screwed in, thus preventing electrolyte liquid flowing out.

The drain-off pin 208 made of Ag/AgCl passes through this stopper 202 and likewise protrudes through the retaining element 196 and is in electrical contact with the electrolyte liquid.

It is advantageous if the bore 190 has a longitudinal groove 210 which receives a guide element 212 which is rigidly connecteo to the retaining element 196, thus preventing twisting of the retaining element 196 when the stopper 202 is screwed in.

However, instead of a flat design of the membrane 194, a tubular membrane 216 may also be used, which is advantageously designed as an ion-selective glass. This embodiment is specifically shown in FIG. 6 at the electrode 184. According to this embodiment, the tubular electrode 216 extends through the electrode body 218, which has fitting cross-bores 220 and 222, into which the tubular electrode is advantageously stuck in. The outer circumference of the tubular electrode is in connection in the region of the bore 224 provided for it at right angles, which is substantially the same as the bore 190 according to FIG. 10, but is drawn down further to form a blind hole, so that the tubular electrode 216 is completely washed by electrolyte liquid around it. In a similar way, the bore 224 is again closed off by a stopper 202 with drain-off pin 208.

In order to make a liquid-tight electrode block 22, the electrodes 180–186 advantageously have, in each case, on one side a bore 226 extending concentrically to the cross-bore 188 or 220, 222 respectively, which takes the form of a blind hole. For purposes of sealing, this bore 226 has an annular groove 228 in the bottom region, into which an O-ring 230 is laid.

The opposite side has a cylindrical elevation 232 which fits together positively with the bore 226 of another electrode and, in assembly, compresses the O-ring 230, sealing off the entire arrangement, as can be seen in FIGS. 4 and 5.

In order to fix the positions of the electrodes 180–186, they are clamped into a holder 234 which consists of a jaw 236 and a further jaw 238, which can be screwed together by a Lock screw 240. The lock screw thereby connects the jaw 238 to a leg of the jaw 236 taken past the rear of the electrodes 180–186. In a corresponding way, these jaws 236 and 238 have a recess 242 and a cylindrical elevation 244 which correspond to the bore 226 and the elevation 212, respectively, of the electrodes according to FIGS. 6 and 10.

Furthermore, drilled through each of these jaws is a cross bore 246 and 248, whcch are flush with the cross-bore 24 of the electrode block and thus form a flow arrangement. Furthermore, these jaws are each provided on their outer side with a connection pipe 250 and 252, to which corresponding tubes can be connected, for example the tubes for the lines 30 and 32.

Furthermore, the clamping jaw 236 may have a vertical bore 254, into which a guide pin 256 can be inserted, with which the electrode block is bolted down onto a housing (not shown).

Moreover, the measuring device according to the invention càn have a conductivity measuring cell, diagrammatically shown in FIG. 5 at the electrode 186. As its conductivity measuring unit 260, this has three graphite disks 262, 264, and 266, each of which is separated from the others by a sealing washer 258. Drilled through all washers, i.e. the LF measuring unit 260, is again a crossbore 270, which is flush with the measuring channel. This cross-bore 270 is in each in direct connection with the LF measuring unit.

Going off from the outer graphite disks 262 and 266 is a common line 272, while the middle graphite disk 264 is connected to the line 274. The two lines 272 and 274 are connected to the electrode connection unit 294, for example in the form of the line 92.

The measurment of conductivity is performed in the usual way by means of measuring the alternating current resistance at a frequency of 1-10, preferably about 3 kHz.

All electrodes 180-186 in electrode block 22 advantageously consist of transparent plastic glass, for example of polyacrylic glass, and make possible an uninterrupted control of the measuring capillaries, in other words of the flow channel 24, which advantageously has a diameter of about 1 mm.

To protect the high-resistive electrodes 180-186 against electrostatic fields, the electrode block 22 is advantageously sheathed in aluminium apart from the front side, which is realised in the case of this example by the holding apparatus 234.

The front side is advantageously transparent and coated with an electrically conductive overlay, for example an InO overlay.

The standard size of the electrode bodies 186 makes possible an easy exchange and any configuration of the electrodes, for example an Na-K-sensitive or an LF electrode can be arranged next to each other. On the other hand, the configuration may also be as follows: Na,Na,Na, or K,pH,Na.

The compact design of the electrodes 180-186, dispensing with any type or form of tube connection pipe, makes a short measuring channel possible, so that, even with three parameters to be measured at the same time, the sample quantity remains small and the blockage reliability great due to the use of a relatively wide capillary as flow channel 24. The choice of electrodes is determined by the intended application and is in itself uncritical. Thus, the usual ion-selective electrodes, for example glass electrodes, plastic electrodes of PVC, which contain an ionselective material, for example valinomycin, or the like may be used. The bores 190 and 224 are filled with the usual electrolyte solutions, for example sodium and/or potassium chloride solutions.

FIGS. 7-10 show the special embodiment of a reference electrode 280 in connection with an electrode block 282. As well as the reference electrode 280, this electrode block has several electrodes 284-288, which correspond in shape ano arrangement to the previously described electrodes 180-186, so that reference is made to these.

Figure 7:
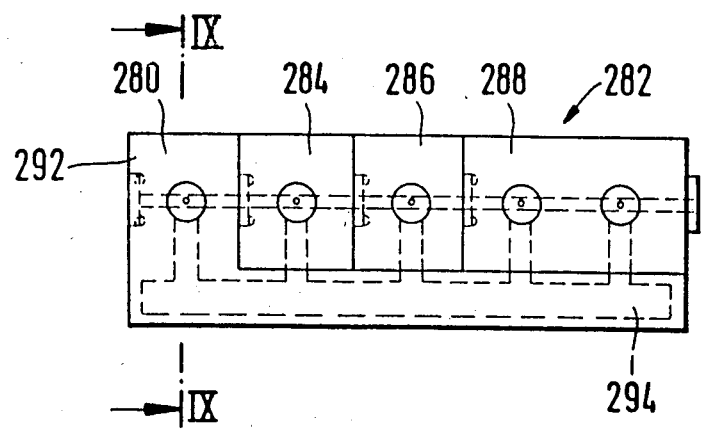
FIG. 7 shows a plan view of the reference electrode which is built into the electrode block.
Figure 8:
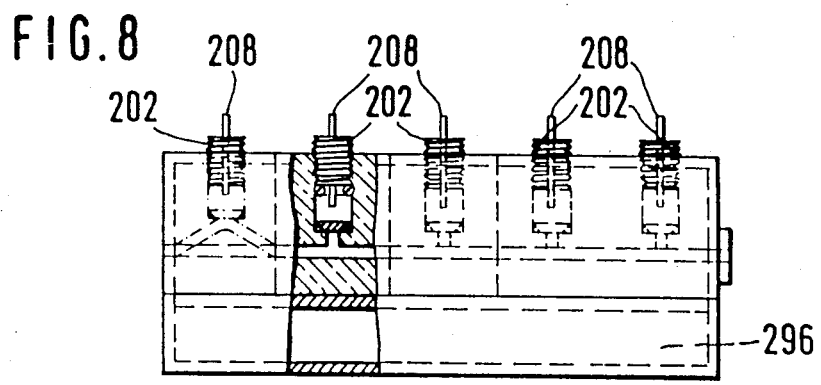
FIG. 8 shows a front view of the reference electrode.
Figure 9:
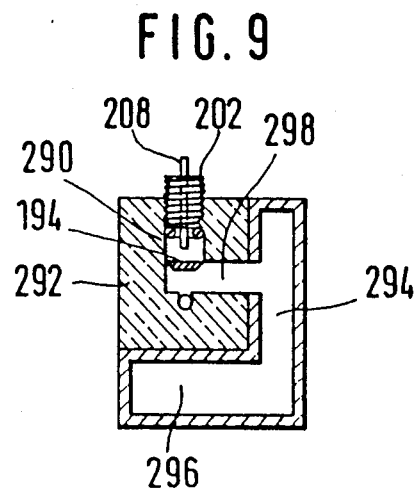
FIG. 9 shows a section through the reference electrode according to FIG. 7 along the line IX—IX.

Only the reference electrode 280 is of special design, which can be seen in particular from FIGS. 7-9. The reference electrode has again a vertical bore 290, which extends into the cuboid electrode body 292. Adjoining this electrode body 292 is a hollow leg 294, which covers the front side of the electrodes 284-288 and is in flow connection with a hollow leg 296 which is arranged bentoff at right angles in the horizontal and clasps under all electrodes. The hollow leg 294 is in turn in flow connection with the bore 290 via a flow channel 298, with the consequence that all hollow legs 294 and 296 can be filled with the reference electrolyte solution through the bore 290.

This reference electrode otherwise corresponds in its structure to the electrode according to FIG. 10, the membrane 194 being designed in such a way that it allows the smallest possible quantities of liquid to pass in either direction.

Thus, the electrolyte-filled plates or hollow legs 294 and 296 surround the measuring electrodes 284-288 at the front and underneath and, due to the good electrical conductivity of the inner electrolyte, the high-resistive, interference-sensitive measuring electrodes 284-288 are screened from external electrical fields up to a limit frequency, from which no more ionic shifts are observed, and consequently nor can they interfere any longer.

Such an enclosed reference electrode 280 only has a maximum service life of only about 6 weeks to about 6 months. The cause of the limitation to its service life lies in the contamination of the membrane 194 with impurity ions and deposits in the decreasing concentration of the inner electrolyte due to the exchange via the membrane 194 and in the deterioration of the properties of the AgCl contact in the drain-off pin 208. The reference electrode 280 shown in FIGS. 7-10 can be well maintained however, although it is of relatively complicated design, as the wear parts are easy to exchange, while the electrode body 292 can continue to be used. The membrane 194 can be exchanged by unscrewing the stopper 202 and removing the retaining or insert element 196. The membrane 194 is then free on the seating and can be removed and replaced by a new membrane. Subsequently, the retaining element 196 and the stopper 202 are replaced, the position of the latter being fixed by screwing in the retaining element 196, and thus fixing the position of the membrane 194. In a similar way, the inner electrolyte solution can be exchanged by removing the stopper 202 and withdrawing the liquid through an injection needle ano replacing it by a fresh liquid.

We claim:

1. A measuring device for determination of the activity or the concentration of ions in solution comprising:
    a flow channel (24) having a reference electrode and at least one measuring electrode, said flow channel having a first end (26) and a second end (28);
    a first line (30) connecting said first end of said flow channel to at least one calibrating liquid container (50, 52) through first valve means (44, 46, 48);
    first pumping means (34) interposed in said first line (30) between said first valve means (44, 46, 48) and said first end (26) of said flow channel (24);
    a waste line (54) connected to said first line adjacent said first end (26) of said flow channel (24), said waste line having second pumping means and second valve means (58);
    a sample feed line (32) connected to said second end (28) of said flow channel for providing a sample to said flow channel;
    first and second sensors (70, 72) arranged in said first and second ends of said flow channel, respectively, for detecting the flowing fronts of liquids, said sensors comprising electro-optical sensors capable of discriminating between the presence and absence of liquids and among liquids of differing properties;
    control means coupled to said sensors, pumping means, and valve means for controlling said pumping means and valve means so that, sequentially, a calibrating liquid is fed from said calibrating liquid container (50, 52) through said first line (30) and said flow channel via said first end by means of said first pumping means (34) until the flowing front of said calibrating liquid is detected by said second sensor (72), the calibrating liquid is removed from said flow channel out of said first end by said second pumping means and delivered to said waste line, a sample is fed from said sample container (68) through said sample feed line (32) and said flow channel (24) via said second end by means of said second pumping means until the flowing front of said sample is detected by said first sensor (70) and, the sample is removed from said flow channel out of said first end by said second pumping means and delivered to said waste line.

2. A measuring device according to claim 1 wherein said second pumping means has at least the same displacement rate as said first pumping means.

3. A measuring device according to claim 1 wherein said first and second pumping means comprise a peristaltic tube pump.

4. A measuring device according to claim 1 further including a third sensor (74) in said first line (30) intermediate said first pumping means and the connection of said waste line (54) to said first line (30).

5. A measuring device according to claim 1 further including a third sensor (76) in said waste line (54) downstream of said second pumping means.

6. A measuring device according to claim 4 further including a third sensor (76) in said waste line (54) downstream of said second pumping means.

7. A measuring device as claimed in claim 1 wherein said sample feed line (32) includes an adapter (64) for receiving an exchangeable aspiration cannula.

8. A measuring device as claimed in claim 1 wherein the end of said first line not connected to said flow channel contains a plurality of branches extending from a branch point, two of said branches being connected to calibrating solution containers, a third of said branches comprising a vent, each of said branches containing a valve (44, 46, 48).

9. A measuring device as claimed in claim 1 wherein said sensors comprise electro-optical sensors formed of a photodiode (160) and a phototransistor (162) arranged in a light barrier housing (146) on opposite sides of said lines.

10. A measuring device as claimed in claim 4 wherein said sensors comprise electro-optical sensors formed of a photodiode (160) and a phototransistor (162) arranged in a light barrier housing (146) on opposite sides of said lines.

11. A measuring device as claimed in claim 5 wherein said sensors comprise electro-optical sensors formed of a photodiode (160) and a phototransistor (162) arranged in a light barrier housing (146) on opposite sides of said lines.

12. A measuring device as claimed in claim 1 wherein said flow channel extends through an electrode block (22) having a plurality of electrode elements (180, 182, 184, 186), each of said electrode elements having on one side a cylindrical projection concentric to said flow channel and on the other side a cylindrical bore (226) for receiving the cylindrical projection of an djacent electrode element.

13. A measuring device as claimed in claim 12 wherein said cylindrical bore has an annular groove (228) for receiving a sealing O-ring (230), and wherein said electrode block is clamped in a holder (234) containing said elements and comprising a first jaw (236) and a second jaw (238), drawn together by a locking screw (240).

14. A measuring device as claimed in claim 1 wherein at least one of said electrode elements includes a bore (224), the axis of which extends transverse to the axis of said flow channel (24), a stppper (202) for closing off said bore, a drainoff pin (208) passing through said stopper (202), and an electrode (216, 194) for separating said bore (224) from said flow channel (24), said bore being filled with an electrolyte liquid into which the drain-off pin (208) dips.

15. A measuring device as claimed in claim 1 wherein said reference electrode (208) has a chamber filled with electrolyte liquid extending on the underside and the front side of said measuring electrodes (284-288) to form horizontal and vertical hollow legs (294 and 296) for screening said measuring electrodes (284-288) against high resistance interference fields.

* * * * *